(12) United States Patent
Prete et al.

(10) Patent No.: US 9,791,369 B2
(45) Date of Patent: Oct. 17, 2017

(54) VISUALIZATION KIT COMPRISING A FLUORESCENT AGENT AND A CYANOACRYLATE, AND METHOD OF COFUMIGATION OF A FLUORESCENT AGENT AND A CYANOACRYLATE

(75) Inventors: Cosimo Prete, Villeneuve D'ascq (FR); Pierre Audebert, Cachan (FR); Laurent Galmiche, Cachan (FR); Clemence Allain, Cachan (FR)

(73) Assignees: CRIME SCIENCE TECHNOLOGY, Loos (FR); ECOLE NORMALE SUPERIEURE DE CACHAN, Cachan (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 1179 days.

(21) Appl. No.: 14/003,957

(22) PCT Filed: Mar. 6, 2012

(86) PCT No.: PCT/FR2012/050462
§ 371 (c)(1),
(2), (4) Date: Sep. 9, 2013

(87) PCT Pub. No.: WO2012/120234
PCT Pub. Date: Sep. 13, 2012

(65) Prior Publication Data
US 2014/0004620 A1 Jan. 2, 2014

(30) Foreign Application Priority Data
Mar. 7, 2011 (FR) ...................................... 11 51828

(51) Int. Cl.
*G01N 21/64* (2006.01)
*C07D 257/08* (2006.01)
(Continued)

(52) U.S. Cl.
CPC ........... *G01N 21/64* (2013.01); *C07D 257/08* (2013.01); *C07D 403/04* (2013.01); *A61B 5/1172* (2013.01)

(58) Field of Classification Search
CPC .................................................... C07D 257/08
See application file for complete search history.

(56) References Cited

U.S. PATENT DOCUMENTS

| 4,504,408 A | 3/1985 | Morton |
| 4,882,195 A * | 11/1989 | Butland ............... A61B 5/1172 427/1 |

(Continued)

FOREIGN PATENT DOCUMENTS

WO    2008/020951    2/2008

OTHER PUBLICATIONS

International Search Report dated Jun. 1, 2012; corresponding to PCT/FR2012/050462.

(Continued)

*Primary Examiner* — Yelena G Gakh
*Assistant Examiner* — Michelle Adams
(74) *Attorney, Agent, or Firm* — Young & Thompson

(57) ABSTRACT

A visualization kit includes (i) a cyanoacrylate and (ii) a fluorescent agent containing at least one tetrazine of formula 1:

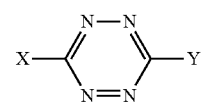

(1)

wherein X and Y represent independently a nonionic, electron-withdrawing group selected from halogens, azide, cyano and O-A-R, in which A represents a single bond or a C1-C4 alkyldiyl and R is alkyl, alkenyl, alkynyl, cycloalkyl or epoxyalkyl, or an aziridine group, which is optionally substituted by alkyl or aryl. A method of cofugation and a (Continued)

method of visualizing traces on a substrate utilizing these components are also presented.

14 Claims, 1 Drawing Sheet

(51) Int. Cl.
    *C07D 403/04*     (2006.01)
    *A61B 5/117*     (2016.01)
    *G01N 33/52*     (2006.01)
    *A61B 5/1172*     (2016.01)

(56) References Cited

U.S. PATENT DOCUMENTS

2005/0143603 A1*   6/2005   Bub ......................... C07C 45/34
                                                                                    562/548
2010/0047433 A1*   2/2010   Shimoda ............... A61B 5/1172
                                                                                      427/1

OTHER PUBLICATIONS

Taniuchi, et al.; "Enzymatic Formation of Catechol From Anthranilic Acid"; Journal of Biological Chemistry; vol. 239; Jul. 1, 1964 pp. 2204-2211.

Therald Moeller, et al.; "Analytical Applications of 8-Hydroxyquinoline Derivatives of Gallium and Thallium"; Analytical Chemistry, vol. 22, No. 5, May 1, 1950; pp. 686-690.

Y-H Gong, et al.; "Synthesis and Physical Chemistry of S-Tetrazines: Which Ones are Fluorescent and Why?" European Journal of Organic Chemistry; vol. 2009, No. 35; Oct. 30, 2009; pp. 6121-6128.

Gilles Clavier, et al.; "S-Tetrazines as Building Blocks for New Functional Molecules and Molecular Materials"; Chemical Reviews; vol. 110, No. 6, Jun. 9, 2010; pp. 3299-3314.

S. Morimoto, et al.; "A New Method to Ehance Visualization of Latent Fingermarks by Sublimating Dyes . . . "; Forensic Science International; vol. 97, 1998, pp. 101-108.

\* cited by examiner

VISUALIZATION KIT COMPRISING A FLUORESCENT AGENT AND A CYANOACRYLATE, AND METHOD OF COFUMIGATION OF A FLUORESCENT AGENT AND A CYANOACRYLATE

FIELD OF THE INVENTION

The invention pertains to a visualization kit comprising a fluorescent agent and a cyanoacrylate, to a method for cofumigation of a fluorescent agent and a cyanoacrylate and the use of this method for the visualization of traces, especially papillary traces.

BACKGROUND OF THE INVENTION

Papillary traces are one of the most effective tools in identifying individuals in criminal investigations. Papillary traces may be classified in three categories: visible traces, impressed traces, and latent traces. In the analysis of a crime scene, the investigators are looking to obtain portable and durable copies of the papillary traces, by making a photograph of them, for example. The visible traces can be photographed directly, and the impressed traces can also be photographed under certain lighting conditions.

The latent traces are the most numerous and the most difficult to lift. This is because they have a low or even zero visibility in direct light and must therefore be made to show up using a variety of methods, by increasing the contrast between the traces and the substrate. The traces are produced by the deposition of a complex mixture of natural secretions from three types of glands: the ecrine and apocrine sweat glands, and the sebaceous glands. The sweat glands produce perspiration and are distributed over the entire body. The palmar and plantar surfaces of the skin are exclusively linked to ecrine glands, whose secretions are evacuated via pores situated on the summit of the papillary ridges. These secretions are composed of inorganic substances such as the following: water (98%), chlorides, sulphates, phosphates, ammonia and metal ions. They also include organic substances such as the following: amino acids, uric acid, lactic acid, urea, sugars, creatinine and choline. The latent traces are therefore originally produced by the deposition of sweat from ecrine glands. They are often contaminated with fats originating from the sebaceous glands: the act of touching the face carries a mixture of sweat and fats onto the surface of the hands.

The techniques of visualization are therefore directed at the constituents produced by the ecrine glands (especially water, amino acids and chlorides), but also to the fatty substances present as a result of contamination.

The use of cyanoacrylates for the visualization of papillary traces is a method universally employed by the forces of order. The technique is simple to execute and particularly effective. Cyanoacrylates are a class of molecules commonly used as glues and often referred to as SUPERGLUE® or CYANOLITE®. In this method, the cyanoacrylates enter into a nucleophilic polymerization reaction. Any site or species sufficiently rich in electrons may act as the initiating nucleophile of the polymerization reaction. More particularly, water or else —COOH functions of fatty acids may act in this way. This polymerization reaction allows the cyanoacrylate in particular to reveal the latent traces, primarily the papillary prints. This reaction takes place by sublimation or fumigation of the cyanoacrylate. The molecules of vapours originating from cyanoacrylate combine with the sudoral deposits to form a chemical chain (polymerization reaction), which colours the ridges of the traces white and at the same time fixes them. This technique is employed effectively to fix the traces present on the majority of both non-porous and semi-porous substrates, and more particularly on flexible or rigid plastics, metals, glass, and varnished, painted or glazed wood, etc.

The main limitation on the technique of cyanoacrylate fumigation is linked to the white colour of the visualization. The contrast between the visualized trace and the substrate on which this trace is found is not always sufficient. In order to reinforce the contrast, the usual solution is to use low-angle lighting, or to apply a fingerprinting powder or else a stain after visualization. A combination of a number of techniques is therefore necessary to obtain a satisfactory result. The use of stains, in the form of powders or solutions, has the advantage of being adaptable to the particular configurations: the nature of the stain and its colour may be selected from a fairly broad range, in order to allow optimum staining of the trace and an effective contrast. Unfortunately, some of these methods degrade DNA, thereby preventing their use before biological material is sought, and do not always offer a satisfactory solution (technical limitation, time, cost, etc.).

Accordingly, the solutions commonly recommended are not all compatible with the subsequent examinations to which the trace or the substrate on which it is deposited may be subjected, and none of them provides an effective solution to the problem of trace resolution in all of the practical cases encountered, especially irrespective of the substrate on which the trace is deposited or of the subsequent examinations.

SUMMARY OF THE INVENTION

The present inventors have found, unexpectedly and surprisingly, that the various problems associated with the prior techniques could be resolved by virtue of the use of a visualization kit comprising a fluorescent agent and a cyanoacrylate.

The present invention accordingly relates to a visualization kit comprising a fluorescent agent and a cyanoacrylate, to a method of cofumigation of a fluorescent agent and a cyanoacrylate, and to the use of this method for the visualization of traces, especially papillary traces.

DETAILED DESCRIPTION OF THE INVENTION

Figure 1:
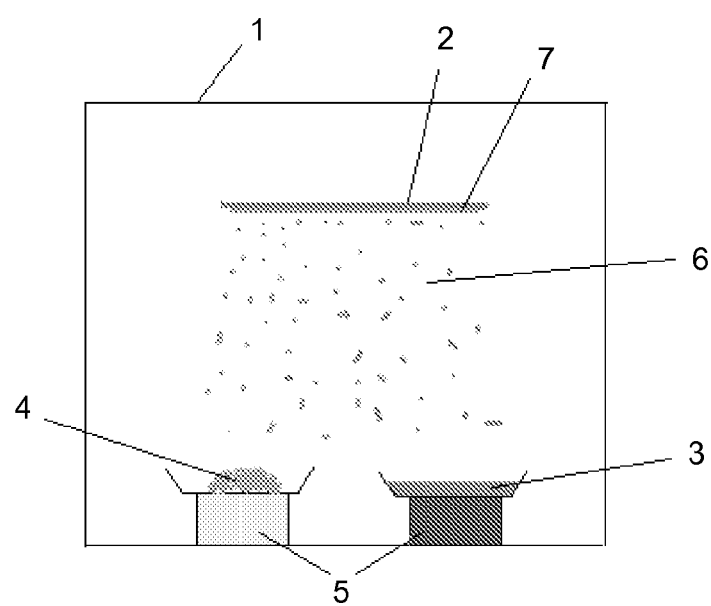
FIG. 1 is a diagrammatic representation of the implementation of the cofumigating step of a method for visualizing traces according to the present invention.

According to a first aspect, the invention provides a visualization kit comprising:

(A) a cyanoacrylate; and
(B) a fluorescent agent having a molecular weight of less than 400 g·mol$^{-1}$, preferably from 100 to 300 g·mol$^{-1}$, more preferably from 130 to 250 g·mol$^{-1}$; a sublimation temperature of less than 200° C., preferably of 50° C. to 150° C., more preferably of 60° C. to 120° C.; and an extinction coefficient of less than 2950 L·mol$^{-1}$·cm$^{-1}$, preferably from 200 to 2950 L·mol$^{-1}$·cm$^{-1}$, more preferably from 1000 to 2950 L·mol$^{-1}$·cm$^{-1}$.

A "visualization kit" is an article comprising the elements (A) and (B), which may be in separate form, in the form of a premix for dilution or in the form of a ready-to-use mixture.

In one particular embodiment, the invention also relates to a composition comprising (A) a cyanoacrylate and (B) a fluorescent agent having a molecular weight of less than 400 g·mol$^{-1}$, preferably from 100 to 300 g·mol$^{-1}$, more preferably from 130 to 250 g·mol$^{-1}$; a sublimation temperature of less than 200° C., preferably of 50° C. to 150° C., more preferably of 60° C. to 120° C.; and an extinction coefficient of less than 2950 L·mol$^{-1}$·cm$^{-1}$, preferably of 200 to 2950 L·mol$^{-1}$·cm$^{-1}$, more preferably of 500 to 2950 L·mol$^{-1}$·cm$^{-1}$. The composition according to the invention may comprise a solvent.

The sublimation temperature is determined by thermogravimetric analysis (TGA). The temperature ramp used is of 1° C./min.

The molar extinction coefficient is defined as the ratio between the absorptivity and the concentration of a chemical entity which absorbs within a given medium, for example dichloromethane (expressed in L·mol$^{-1}$·cm$^{-1}$) and is determined by UV-Visible absorption spectroscopy, from 250 to 800 nm (measuring the absorbance of solutions with known concentrations in cells of known optical path length).

The fluorescent agent advantageously has a brightness of more than 200 L·mol$^{-1}$·cm$^{-1}$, preferably of 250 to 4000 L·mol$^{-1}$·cm$^{-1}$. The brightness is defined as the product of the molar extinction coefficient at the selected excitation wavelength and of the quantum fluorescence yield, the molar extinction coefficient being determined by UV-visible absorption spectroscopy, from 250 to 800 nm, and the quantum fluorescence yield being determined by fluorescence emission spectroscopy, in accordance with the customary protocols known to the skilled person. The quantum fluorescence yield of the fluorescent compound being looked at is determined by comparing the fluorescence intensity of a solution of this compound with the fluorescence intensity of an isoabsorbent solution of a reference fluorophore (of known quantum yield). The fluorescence intensity of the fluorescent compound under study is determined on the basis of a solution of this compound in dichloromethane, and the excitation wavelength is selected such that, at this given wavelength, the absorption of the said compound under study is greater than or equal to 10% of it absorption maximum in a UV-visible absorption spectrum. The fluorescence intensity of the reference fluorophore is determined at the same given wavelength, on the basis of a solution of the reference fluorophore in the solvent for which it is referenced. The solutions of the compound under study and of the reference fluorophore must be isoabsorbent, meaning that the concentrations are adjusted so that the two solutions exhibit equivalent absorption at the given excitation wavelength.

The fluorescent agent is advantageously an organic fluorescent agent. An organic fluorescent agent in the sense of the present invention is any organic molecule which per se has fluorescent properties. This excludes, for example, inorganic materials and organic or inorganic chelates, such as lanthanide, thorium or yttrium chelates.

In one particular embodiment the fluorescent agent is a tetrazine of formula 1:

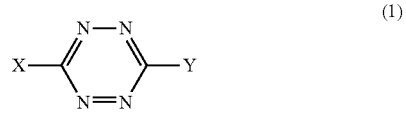

in which X and Y represent independently
a nonionic, electron-withdrawing group, which may be substituted by a polymerizable group;
an aziridine group, which is optionally substituted by alkyl or aryl;
X and Y cannot represent an amino group or any other group bonded to the tetrazine ring by a nitrogen atom, other than the said aziridine group; and
X and Y cannot represent a thio group or any other group bonded to the tetrazine ring by a sulphur atom.

The term "nonionic, electron-withdrawing group" in the sense of the present invention means any group having an electron-withdrawing inductive effect, with the exception of ionic groups; more particularly halogens and neutral groups composed of a divalent or trivalent heteroatom such as oxygen, especially —O-A-R in which A represents a single bond or a $C_1$-$C_4$ alkyldiyl and R is alkyl, alkenyl, alkynyl, cycloalkyl, aryl or epoxyalkyl.

The term "halogen" in the sense of the present invention means the atoms F, Cl, Br or I, more particularly F and Cl.

The term "alkyl" in the sense of the present invention means any linear or branched alkyl group, more particularly alkyl groups containing 1 to 6 carbon atoms, especially the groups methyl, ethyl, n-propyl, isopropyl or isobutyl.

The term "alkenyl" in the sense of the present invention means any alkenyl group comprising at least one double bond, more particularly alkenyl groups containing 2 to 6 carbon atoms, especially the groups ethenyl or allyl.

The term "alkynyl" in the sense of the present invention means any alkynyl group comprising at least one triple bond, more particularly alkynyl groups containing 2 to 6 carbon atoms, especially the groups ethynyl and propargyl.

The term "cycloalkyl" in the sense of the present invention means any cycloalkyl group, more particularly monocyclic, bicyclic or tricyclic cycloalkyl groups, each cyclic moiety containing 5 or 6 carbon atoms, especially the groups cyclohexyl or adamantanyl.

The term "aryl" (Ar) in the sense of the present invention means any aryl group, more particularly monocyclic, bicyclic or tricyclic aryl groups, each cyclic moiety containing 5 or 6 carbon atoms, especially the groups benzyl or naphthalenyl.

The term "epoxyalkyl" in the sense of the present invention means any epoxyalkyl group, more particularly epoxyalkyl groups containing 2 to 6 carbon atoms, especially the groups 2,3-epoxypropyl or 3,4-epoxybutyl.

The term "$C_1$-$C_4$ alkyldiyl" in the sense of the present invention means any bivalent alkyl group containing 1 to 4 carbon atoms, especially the groups —$CH_2$— and —($CH_2$)$_2$—.

By "aziridine" group is meant the three-membered cyclic group —$NC_2H_4$. The carbons of this group may be substituted by an alkyl or aryl group.

By "polymerizable group" in the sense of the present invention is meant a group possessing a double bond, a triple bond or a heterocycle.

According to one particular embodiment, X and Y are selected independently in the group consisting of halogen, azide, cyano and —O-A-R in which A represents a single bond or a $C_1$-$C_4$ alkyldiyl, preferably —$CH_2$—, and R is alkyl, alkenyl, alkynyl, cycloalkyl, aryl or epoxyalkyl.

According to another particular embodiment, X is selected from the group consisting of halogen, azide, cyano and —O-A-R' in which A represents a single bond or a $C_1$-$C_4$ alkyldiyl, preferably —$CH_2$—, and R' is alkyl, cycloalkyl or aryl, and Y is —OR" in which R" is alkenyl, alkynyl or epoxyalkyl.

Each of the substituents X and Y advantageously comprises not more than 12 carbon atoms.

According to one particular embodiment, the tetrazine of formula 1 is selected from the group consisting of 3,6-dichloro-1,2,4,5-tetrazine, 3-chloro-6-methoxy-1,2,4,5-tetrazine, 3-chloro-6-ethoxy-1,2,4,5-tetrazine, 3,6-dimethoxy-1,2,4,5-tetrazine, 3-chloro-6-(prop-2-enyloxy)-1,2,4,5-tetrazine, 3-chloro-6-(prop-2-ynyloxy)-1,2,4,5-tetrazine, 3-chloro-6-(adamant-2-yloxy)-1,2,4,5-tetrazine, 3-chloro-6-(adamant-1-ylmethoxy)-1,2,4,5-tetrazine, 3-chloro-6-(naphthalen-1-yloxy)-1,2,4,5-tetrazine and 3-chloro-6-(3-epoxybutyloxy)-1,2,4,5-tetrazine, the product of formula

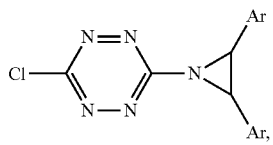

and mixtures thereof.

Table 1 presents the features of some of these compounds:

TABLE 1

| Compound | Molecular weight (g · mol⁻¹) | Sublimation temperature (° C.) | Extinction coefficient (L · mol⁻¹ · cm⁻¹) | Brightness* (L · mol⁻¹ · cm⁻¹) |
|---|---|---|---|---|
| 3,6-dichloro-1,2,4,5-tetrazine | 150.95 | 76 | 1900 | 270 |
| 3-chloro-6-methoxy-1,2,4,5-tetrazine | 146.54 | 86 | 2905 | 1100 |
| 3-chloro-6-ethoxy-1,2,4,5-tetrazine | 160.56 | 87 | 2900 | 780 |
| 3,6-dimethoxy-1,2,4,5-tetrazine | 142.12 | 99 | 2935 | 320 |
| 3-chloro-6-(adamant-1-ylmethoxy)-1,2,4,5-tetrazine | 280.75 | 138 | 2950 | 1180 |

*measured in dichloromethane

The cyanoacrylate used in the visualization kit according to the invention may be any cyanoacrylate which is commonly known and is available commercially for application as an instant adhesive. More particularly the cyanoacrylates which may be used in the visualization kit according to the invention are the cyanoacrylates of formula 2:

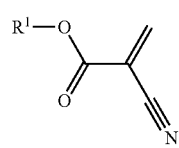

(2)

in which $R^1$ is alkyl, alkenyl, alkynyl, cycloalkyl or aryl, and $R^1$ may be optionally substituted by a halogen or a hydroxyl group. For example, the cyanoacrylate is selected from the group consisting of methyl 2-cyanoacrylate, ethyl 2-cyanoacrylate, propyl 2-cyanoacrylate, butyl 2-cyanoacrylate, allyl 2-cyanoacrylate, methoxyethyl 2-cyanoacrylate, ethoxyethyl 2-cyanoacrylate, 2-chloroethyl 2-cyanoacrylate, cyclohexyl 2-cyanoacrylate, ethoxycarbonylmethyl 2-cyanoacrylate, trifluoroethyl 2-cyanoacrylate and mixtures thereof.

Particularly preferred cyanoacrylates are cyanoacrylates having a low viscosity. According to one particular embodiment, the cyanoacrylate is selected from lower alkyl (C1-C4 alkyl) cyanoacrylates, especially ethyl 2-cyanoacrylate or methyl 2-cyanoacrylate.

The compounds (A) and (B) may be present in the visualization kit separately or in the form of a mixture.

Advantageously, when the fluorescent agent is 3-chloro-6-methoxy-1,2,4,5-tetrazine or 3-chloro-6-(prop-2-ynyloxy)-1,2,4,5-tetrazine, it is present in a form separate from the cyanoacrylate, meaning that the two products are not in contact with one another.

According to another embodiment, the fluorescent agent and the cyanoacrylate are in a mixture, and the visualization kit is then a visualizing composition comprising each of the compounds (A) and (B).

This embodiment is particularly suitable when the fluorescent agent is 3-chloro-6-ethoxy-1,2,4,5-tetrazine. According to one advantageous embodiment, the visualizing composition comprises 3-chloro-6-ethoxy-1,2,4,5-tetrazine and ethyl 2-cyanoacrylate.

In the visualization kit or the visualizing composition, the ratio by weight of the compounds (A) and (B) is from 100:1 to 500:1. In a first alternative, the ratio (A):(B) is preferably from 200:1 to 400:1. In a second alternative, the ratio (A):(B) is preferably from 100:1 to 200:1.

According to another aspect, the invention relates to a method for cofumigation of a cyanoacrylate (A) and a fluorescent agent (B) as defined above.

This method allows the application of a fluorescent polymeric layer to a surface.

This method is unique for the ease of sublimation of the fluorescent agent (B), especially of tetrazines. The reason is that owing to their relatively high or even very high sublimation temperature, the usual organic stains are degraded on fumigation. Conversely, the fluorescent agent (B) according to the invention has a relatively low sublimation temperature, a unique feature for an organic stain, which it owes primarily to its low molecular weight. It is therefore possible to cofumigate a cyanoacrylate ester and the fluorescent agent of the invention without the latter being degraded.

The cyanoacrylate (A) and the fluorescent agent (B) employed in the method according to the invention are as defined above in connection with the visualization kit.

The method of cofumigation according to the invention involves the simultaneous fumigation of the cyanoacrylate (A) and of the fluorescent agent (B) and the application of the fluorescent polymer thus formed to a surface.

The cofumigation method is performed under conditions such that the cyanoacrylate (A) and the fluorescent (B) are able to vaporize or sublime while at the same time these compounds are not degraded. The cofumigation temperature will be readily determined by the skilled person in dependence on the vaporization or sublimation temperatures of the cyanoacrylate and fluorescent agent that are used. Separate temperatures may be employed if necessary. However, preference will be given to employing a tetrazine and a cyanoacrylate that have compatible sublimation or vaporization temperatures, in other words sublimation or vaporization temperatures that do not give rise to the decomposition of the other compound. For example, cofumigation is performed between 80 and 120° C. The duration of cofumigation is such that it allows the application of a fluorescent polymeric layer to the surface of the substrate, more particularly to the traces present on the substrate. The cofumigation time is typically greater than 5 minutes, and is preferably between 10 and 30 minutes. The cyanoacrylate (A) and the fluorescent agent (B) are used simultaneously in the cofumigation but may be present in the form of two separate compounds (A) and (B). Preference, however, will be given to implementing the cofumigation from a mixture of the compounds (A) and (B). The reason is that current fumigation devices do not often possess heating means that allow simultaneous cofumigation of two separate compounds, especially not at separate temperatures. Furthermore, it is easier to obtain simultaneous fumigation from a mixture than to carry out cofumigation of the compounds separately. Lastly, the cofumigation of the compounds (A) and (B) from a mixture thereof gives a more uniform deposit. It is nevertheless essential that in the case of cofumigation from a mixture of the compounds (A) and (B), these compounds have a closely situated vaporization or sublimation temperature, typically of between 80 and 120° C. The weight ratio between the amount of cyanoacrylate (A) and the amount of fluorescent agent (B) is between 100:1 and 500:1, preferably between 100:1 and 200:1.

This cofumigation method gives rise to a nucleophilic polymerization reaction which is initiated by any site or species sufficiently rich in electrons. More particularly, water may act in this vein. Accordingly, in accordance with one advantageous embodiment, the method according to the invention is conducted in a moist atmosphere, especially with a degree of humidity of the ambient air of at least 70%, preferably 80%. The ease of implementing this method, and the exceptional hold of the coating, owing to the well-known adhesion properties of cyanoacrylate esters, makes this a method of choice for the production of highly resistant fluorescent coatings, more particularly for objects with complex geometry.

Owing to the good quality of the coating formed, and its fluorescence, the method of the invention may be employed on any type of substrate, including porous substrates. This method is therefore applicable irrespective of the type of substrate, such as flexible or rigid plastics, metal, glass, varnished, painted or glazed wood, or the epidermis (skin).

The method according to the invention may visualize traces which are on a substrate, especially latent papillary traces. The invention therefore likewise provides for the use of the cofumigation method described above for the visualization of traces, especially of latent papillary traces on a substrate. This process may be applied to various samples composed of different kinds of substrates that are commonly present at crime scenes and that contain latent papillary traces, for example fingerprints and palm prints present on samples of glass (bottle, laboratory slide), plastic (rubbish bag, freezer bag, cellophane, compact disc) or samples provided with a metallic surface (small beverage can), or else at the crime scene itself when the latter is a closed space, for example a room.

In one particular embodiment, the invention provides a method for visualizing traces on a substrate, comprising the steps of:
  presenting the said substrate bearing traces to a device comprising means of fumigation and containing a cyanoacrylate (A) and a fluorescent agent (B) as defined above;
  cofumigating the compounds (A) and (B) by the method as defined above with the aid of the said device, to give a fumigated substrate;
  submitting the said fumigated substrate to ultraviolet light.

The method for visualizing traces according to the invention advantageously comprises the steps of:
  presenting the said substrate bearing traces to a device comprising means of fumigation and containing a cyanoacrylate (A) and a tetrazine (B) of formula 1 as defined above;
  implementing the cofumigation method as described above by the said device, to give a fumigated substrate;
  submitting the said fumigated substrate to ultraviolet light.

This visualization method may be implemented using various devices comprising means of fumigation that are well known to the skilled person, especially a laboratory fumigation device (such as a UCV 1000 fumigating cabin sold by Foster & Freeman) for the laboratory analysis of objects collected at crime scenes, a portable fumigation device 35 (CYANOWAND®) for localized analysis at a crime scene, or a device for fumigating an entire room (SUPERFUME® sold by Foster & Freeman) for the complete analysis of an indoor crime scene. Depending on the particular case, therefore, the substrate may be an object, a part of an object or of a surface, or an entire room, including all of the walls, floor, ceiling, furniture or any object located therein.

The traces may be latent papillary traces.

The cyanoacrylate (A) and the fluorescent agent (B) are as defined before in relation to the visualization kit.

Before the cofumigation method is implemented, more particularly when it is implemented in a fumigating cabin, the atmosphere is humidified in order to promote the initiation of the nucleophilic polymerization reaction. The atmosphere is advantageously humidified to a degree of humidity of at least 70%, preferably 80%.

The amount of cyanoacrylate (A) and of fluorescent agent (B) to be used for the method for visualizing traces according to the invention is dependent on a number of parameters such as the volume to be fumigated (for example the volume of the fumigation cabin or of the room to be fumigated), the duration of the fumigating cycle, the volume and the surface area of the objects subjected to fumigation, or the degree and the quality of the expected visualization.

Detection of the traces by ultraviolet radiation takes place at a wavelength of between 250 and 370 nm, preferably at around 365 nm or 312 nm, with the aid of suitable illumination, for example a standard laboratory 365 nm or 312 nm lamp or a 10 W 365 nm or 312 nm neon tube. Filtered light of between 450 and 535 nm, preferably of around 515 nm, also provides detection of said traces.

In a first embodiment, the method for visualizing traces on a substrate according to the invention comprises the steps of:
introducing said substrate bearing traces into a fumigation cabin containing a cyanoacrylate (A) and the fluorescent agent (B) as defined above;
cofumigating the compounds (A) and (B) according to the method as described above, to give a fumigated substrate;
subjecting the said fumigated substrate to ultraviolet light.

The fumigation cabin is hermetic. It has a device for controlling the ambient humidity. It is equipped with at least one vessel whose temperature can be regulated. According to one particular embodiment, it is provided with two vessels each independently having a device for regulating the temperature.

It may also be equipped with a device for decontamination of biological traces, so as to prevent any contamination of the substrate under analysis and to preserve the latter for a possible sequent DNA search.

The amount of product deposited by fumigation must also be able to be controlled with a certain degree of precision. For this purpose, a control object is generally introduced into the fumigation cabin with the substrate for analysis, to serve as an indicator for the fume exposure time.

FIG. 1 is a diagrammatic representation of the implementation of the cofumigating step of the method for visualizing traces according to the first embodiment of the method of the invention for visualizing traces (the case of a fumigation cabin having two vessels). In this embodiment, the substrate 2 is introduced into the chamber of the fumigation cabin 1. The cyanoacrylate 3 and the fluorescent agent 4 are disposed in vessels 5. In the cofumigation step, the cyanoacrylate 3 and the fluorescent agent 4 are vaporized or sublimed simultaneously under the effect of the temperature, and form a mixture of vapours 6. In contact with the substrate 2, and especially with traces present on the substrate, this vapour mixture 6 forms a fluorescent coating 7 composed of a cyanoacrylic polymer incorporating molecules of fluorescent agent.

In a second embodiment, the method for visualizing traces on a substrate according to the invention comprises the steps of:
presenting the said substrate bearing traces to an individual, portable fumigation device containing a cyanoacrylate (A) and the fluorescent agent (B) as defined above;
cofumigating the compounds (A) and (B) by means of the portable fumigation device according to the method as described above, to give a fumigated substrate;
subjecting the said fumigated substrate to ultraviolet light.

In a third embodiment, the method for visualizing traces in a room according to the invention comprises the steps of:
providing the fumigation device, containing a cyanoacrylate (A) and the fluorescent agent (B) as defined above, in a closed room;
cofumigating the compounds (A) and (B) by means of the fumigation device, to give a fumigated room;
subjecting the same fumigated room to ultraviolet light.

By the application of the method according to the invention, the fluorescent agent is directly incorporated into the cyanoacrylate deposit. The traces visualized on the substrate may therefore be observed in particular under ultraviolet radiation adapted for the fluorescence characteristics of the fluorescent agent used, for example to a wavelength of between 300 and 370 nm, more particularly 365 nm or 312 nm, to offer optimum contrast. The method of the invention therefore effectively visualizes any latent papillary trace in a single step. The use of stains or of fingerprinting powders after visualization is therefore no longer necessary. In contrast to the use of stains, whether fluorescent or otherwise, subsequent to visualization, which necessitates a thermal aftertreatment for producing the deposit of the stain or for enhancing the adhesion of the stain to the acrylate deposit, the method of the invention makes it possible to limit the operations required for the visualization of the traces and hence to guarantee a maximum of compatibility in the context of DNA search on the substrate, since the fluorescent agent (B), especially the tetrazines of formula 1, do not react with the DNA which may be present on the substrate.

One of the key advantages of the method of the invention, therefore, is that of preserving the DNA molecule. This represents a major concern for criminal investigations, in which scientific investigation techniques are increasingly demanding and where the complementarity and compatibility of the methods is required.

Furthermore, the cofumigation method according to the invention produces selective fluorescence of the traces to be visualized. The assumption, without being tied to any one theory, is that the fluorescent agent reacts with the cyanoacrylate in such a way that the fluorescent agent is bonded to the cyanoacrylate deposit. Consequently, the fluorescence of the cyanoacrylate deposits is persistent, whereas the fluorescence of the deposits of fluorescent agent in free form around the traces disappears rapidly because of the high volatility of the fluorescent agent. The result is a facilitated distinction between the said traces to be visualized, which are fluorescent, and the substrate, which is non-fluorescent. Conversely, when the deposit is obtained by impregnation of the cyanoacrylate deposit (for example an aftertreatment of a fluorescent stain or cofumigation with a fluorescent agent that does not react with cyanoacrylate), the fluorescence appears both on the cyanoacrylate deposit and on the substrate, and the difference in contrast between the traces to be visualized and the substrate is much less.

The deposit obtained is also particularly stable in terms of the fluorescence. The reason, since the fluorescent agent is bonded to the cyanoacrylate deposit, is that the deposit does not sublime and the fluorescence is particularly stable over time. The cyanoacrylate deposit obtained by the method of the invention typically remains fluorescent for at least 6 months. The greater the extent to which the conservation conditions prevent degradation of the fluorescent agent, the more durable the fluorescence of the deposit. Accordingly, the fluorescence of the deposit is particularly stable when it is conserved in the absence of light and humidity.

The invention also relates to the use of the visualization kit according to the invention for implementing the cofumigation method and the method for trace visualization that are described above. The invention also relates to the use of the visualization kit according to the invention for the visualization of traces on a substrate.

The examples which follow further illustrate the method of the invention and its advantage. These examples are given only for illustration and may not be considered to limit the invention.

EXAMPLES

The cyanoacrylate ester used is a cyanoacrylate which is sold by Foster & Freeman under the brand name CYANO- BLOOM®, comprising >99% ethyl 2-cyanoacrylate and <0.02% 1,4-dihydroxybenzene quinol.

Example 1

A mixture of 10 mg of 3-chloro-6-ethoxy-1,2,4,5-tetrazine in 0.375 g of cyanoacrylate was prepared and placed in the vessel of a MCV 1000 fumigation cabin from Foster & Freeman. The sample for analysis, consisting of a drinking glass bearing fingerprints, was introduced into the fumigation cabin. The degree of hygrometry in the fumigation cabin was raised to 80% and the vessel was heated progressively to a temperature of 120° C.

After 15 minutes of fumigation, the sample was removed from the fumigation cabin and was observed under ultraviolet radiation at 312 nm.

Following visualization, particularly clear traces of yellow-orange colour were observed under the ultraviolet radiation at 312 nm for each of the samples analyzed.

These samples were conserved in the absence of light and humidity. Six months after visualization, the traces were observable in just as clear a way under UV radiation at 312 nm.

Example 2

Example 1 was reproduced, using 10 mg of 3-chloro-6-methoxy-1,2,4,5-tetrazine in place of the 10 mg of 3-chloro-6-ethoxy-1,2,4,5-tetrazine, but placing the tetrazine and the cyanoacrylate in two separate vessels in the fumigation cabin.

The temperature of the vessel containing the cyanoacrylate was heated progressively to 120° C. When its temperature reached approximately 85-95° C., the vessel containing the tetrazine was also heated progressively to 90° C. In this way it was possible to fumigate the two compounds simultaneously.

The samples analyzed were observed under ultraviolet radiation at 312 nm. Particularly clear traces of yellow-orange colour were observed for each sample.

The traces were observable in just as clear a way under UV radiation at 312 nm even six months after their visualization and preservation in the absence of light and humidity.

Example 3

Example 2 was reproduced, using 10 mg of 3-chloro-6-(prop-2-ynyloxy)-1,2,4,5-tetrazine in place of the 10 mg of 3-chloro-6-methoxy-1,2,4,5-tetrazine.

The samples analyzed were observed under ultraviolet radiation at 312 nm. Particularly clear traces of yellow-orange colour were observed for each sample.

The samples were conserved in the absence of light and humidity. Six months after visualization, the traces were observable in just as clear a way under UV radiation at 312 nm.

Example 4

Examples 1 to 3 were reproduced with a mixture of 10 mg of 3-chloro-6-ethoxy-1,2,4,5-tetrazine, 3-chloro-6-methoxy-1,2,4,5-tetrazine or 3-chloro-6-(prop-2-ynyloxy)-1,2,4,5-tetrazine, respectively, in 1 g of cyanoacrylate.

The samples analyzed were observed under ultraviolet radiation at 312 nm. In the same way, particularly clear traces of yellow-orange colour were observed for each sample. These traces were observable just as clearly under UV radiation at 312 nm even six months after their visualization, the samples having been conserved in the absence of light and humidity.

The invention claimed is:

1. A visualization kit comprising:
   (A) a cyanoacrylate; and
   (B) a fluorescent agent comprising at least one tetrazine of formula 1:

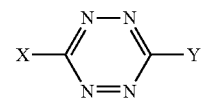

(1)

wherein X and Y represent independently
   a nonionic, electron-withdrawing group selected from halogens, azide, cyano and O-A-R, in which A represents a single bond or a C1-C4 alkyldiyl and R is alkyl, alkenyl, alkynyl, cycloalkyl or epoxyalkyl; or
   an aziridine group, which is optionally substituted by alkyl or aryl.

2. The kit according to claim 1, wherein the fluorescent agent has a molecular weight of less than 400 g·mol$^{-1}$, a sublimation temperature of less than 200° C., and an extinction coefficient of less than 2950 L·mol$^{-1}$·cm$^{-1}$.

3. The kit of claim 1, wherein the fluorescent agent has a brightness of more than 200 L·mol$^{-1}$·cm$^{-1}$.

4. The kit of claim 1, wherein X and Y are selected independently from the group consisting of halogens, azide, cyano and —OR in which R is alkyl, alkenyl, alkynyl, cycloalkyl, and epoxyalkyl.

5. The kit of claim 1, wherein the at least one tetrazine of formula 1 is selected from the group consisting of 3,6-dichloro-1,2,4,5-tetrazine, 3-chloro-6-methoxy-1,2,4,5-tetrazine, 3-chloro-6-ethoxy-1,2,4,5-tetrazine, 3,6-dimethoxy-1,2,4,5-tetrazine, 3-chloro-6-(prop-2-enyloxy)-1,2,4,5-tetrazine, 3-chloro-6-(prop-2-ynyloxy)-1,2,4,5-tetrazine, 3-chloro-6-(adamant-2-yloxy)-1,2,4,5-tetrazine, 3-chloro-6-(adamant-1-ylmethoxy)-1,2,4,5-tetrazine, 3-chloro-6-(3-epoxybutyloxy)-1,2,4,5-tetrazine, the product of formula

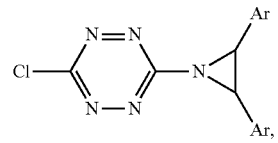

14 and mixtures thereof.

6. The kit of claim 1, wherein the cyanoacrylate is a cyanoacrylate of formula 2:

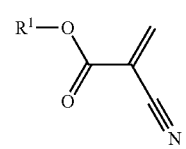

(2)

in which R$^1$ is alkyl, alkenyl, alkynyl, cycloalkyl or aryl, and R$^1$ may be optionally substituted by a halogen or a hydroxyl group.

7. The kit of claim 1, wherein the cyanoacrylate is selected from the group consisting of methyl 2-cyanoacrylate, ethyl 2-cyanoacrylate, propyl 2-cyanoacrylate, butyl 2-cyanoacrylate, allyl 2-cyanoacrylate, methoxyethyl 2-cyanoacrylate, ethoxyethyl 2-cyanoacrylate, 2-chloroethyl 2-cyanoacrylate, cyclohexyl 2-cyanoacrylate, ethoxycarbonylmethyl 2-cyanoacrylate, trifluoroethyl 2-cyanoacrylate and mixtures thereof.

8. A composition, comprising
(A) a cyanoacrylate, and
(B) a fluorescent agent comprising at least one tetrazine of formula 1:

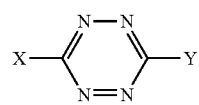
(1)

wherein X and Y represent independently
a nonionic, electron-withdrawing group selected from halogens, azide, cyano and O-A-R in which A represents a single bond or a C1-C4 alkyldiyl and R is alkyl, alkenyl, alkynyl, cycloalkyl or epoxyalkyl; or
an aziridine group, which is optionally substituted by alkyl or aryl.

9. A method, comprising cofumigation of
(A) a cyanoacrylate, and
(B) a fluorescent agent comprising at least one tetrazine of formula 1:

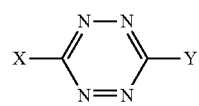
(1)

wherein X and Y represent independently
a nonionic, electron-withdrawing group selected from halogens, azide, cyano and O-A-R in which A represents a single bond or a C1-C4 alkyldiyl and R is alkyl, alkenyl, alkynyl, cycloalkyl or epoxyalkyl; or
an aziridine group, which is optionally substituted by alkyl or aryl.

10. The method of claim 9, wherein the ratio by weight between the amount of the cyanoacrylate and the amount of the fluorescent agent is from 100:1 to 500:1.

11. The method of claim 9, wherein the ratio by weight between the amount of the cyanoacrylate and the amount of the fluorescent agent is from 100:1 to 200:1.

12. The method of claim 9, wherein the cofumigation is carried out at a temperature between 80° C. and 120° C.

13. A method for visualizing traces on a substrate, comprising the steps of:
presenting said substrate bearing traces to a device comprising means of fumigation and containing (A) a cyanoacrylate and (B) a fluorescent agent comprising at least one tetrazine of formula 1:

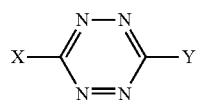
(1)

wherein X and Y represent independently
a nonionic, electron-withdrawing group selected from halogens, azide, cyano and O-A-R in which A represents a single bond or a C1-C4 alkyldiyl and R is alkyl, alkenyl, alkynyl, cycloalkyl or epoxyalkyl; or
an aziridine group, which is optionally substituted by alkyl or aryl;
cofumigating the compounds (A) and (B) by the method as defined in claim 9 with the aid of said device, to give a fumigated substrate; and
submitting said fumigated substrate to ultraviolet light.

14. A method of using the visualization kit of claim 1 for the visualization of traces on a substrate, said method comprising cofumigating the cyanoacrylate and the fluorescent agent in the presence of a substrate bearing traces.

* * * * *